United States Patent
Kosuge et al.

(10) Patent No.: US 10,626,347 B2
(45) Date of Patent: *Apr. 21, 2020

(54) FREE POLYUNSATURATED FATTY ACID-CONTAINING COMPOSITION AND MANUFACTURING METHOD THEREFOR

(71) Applicant: NIPPON SUISAN KAISHA, LTD., Tokyo (JP)

(72) Inventors: Yuhei Kosuge, Tokyo (JP); Hideaki Yamaguchi, Tokyo (JP); Nobushige Doisaki, Tokyo (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/906,602

(22) Filed: Feb. 27, 2018

(65) Prior Publication Data

US 2018/0195021 A1   Jul. 12, 2018

Related U.S. Application Data

(63) Continuation of application No. PCT/JP2016/075444, filed on Aug. 31, 2016.

(30) Foreign Application Priority Data

Aug. 31, 2015 (JP) ................. 2015-170856

(51) Int. Cl.

| C11C 3/00 | (2006.01) |
|---|---|
| C07C 57/12 | (2006.01) |
| A23D 9/007 | (2006.01) |
| C07C 69/58 | (2006.01) |
| A61K 31/201 | (2006.01) |
| A61K 31/202 | (2006.01) |
| A23L 33/12 | (2016.01) |

(52) U.S. Cl.
CPC ............ *C11C 3/00* (2013.01); *A23D 9/007* (2013.01); *A23L 33/12* (2016.08); *A61K 31/201* (2013.01); *A61K 31/202* (2013.01); *C07C 57/12* (2013.01); *C07C 69/58* (2013.01); *A23V 2002/00* (2013.01)

(58) Field of Classification Search
CPC .......... C07C 57/12; C07C 51/09; C11C 1/04; C11C 3/00
See application file for complete search history.

(56) References Cited

U.S. PATENT DOCUMENTS

| 4,615,839 A * | 10/1986 | Seto .................. C07C 57/03 554/176 |
| 5,719,302 A * | 2/1998 | Perrut ................... C11B 3/16 554/191 |
| 5,777,141 A * | 7/1998 | Brunner ................ B01D 15/40 554/175 |
| 8,535,397 B2 * | 9/2013 | D'Addario ............... C11B 1/10 435/134 |
| 8,957,231 B2 | 2/2015 | Sepulveda Reyes et al. |
| 9,062,275 B2 | 6/2015 | Cela Lopez |
| 2004/0236128 A1 | 11/2004 | Rubin |
| 2013/0150602 A1 * | 6/2013 | Kelliher ................. C07C 51/41 554/154 |
| 2014/0005425 A1 | 1/2014 | Harting Glade et al. |
| 2015/0126760 A1 | 5/2015 | Doisaki et al. |
| 2016/0317592 A1 | 11/2016 | Yamaguchi et al. |
| 2017/0000116 A1 | 1/2017 | Sato et al. |
| 2018/0187126 A1 | 7/2018 | Yamaguchi et al. |

FOREIGN PATENT DOCUMENTS

| CA | 2822314 A1 | 7/2012 |
| JP | S60-133094 A | 7/1985 |
| JP | H07-242895 A | 9/1995 |
| JP | H09-238693 A | 9/1997 |
| JP | H10-139718 A | 5/1998 |
| JP | 2002-069475 A | 3/2002 |
| JP | 2004-89048 A | 3/2004 |
| JP | 2007-89522 A | 4/2007 |

(Continued)

OTHER PUBLICATIONS

JP 2007-089522, Tsunoda Motoo, et al., Method for producing fatty acid composition containing specific highly unsaturated fatty acid in concentrated state, 2007, English translation, 20 pages (Year: 2007).*

Nagao, T., et al., Enzymatic purification of dihomo-gamma-linolenic acid from Mortierella single-cell oil, 2007, Journal of Molecular Catalysis B: Enzymatic, vol. 44, pp. 14-19 (Year: 2007).*

Yamamura, Ryuji et al., "High Purification of Polyunsaturated Fatty Acids," Journal of Japan Oil Chemists' Society, 1998, vol. 47, No. 5, pp. 449-456, particularly, p. 450 (w/ English translation).

"Basic Oil Analytical Test Methods", 2013 Edition, 2.4.2.1-2013 Fatty Acid Composition (FID Isothermal Gass Chromatography) established by the Japan Oil Chemists' Society (JOCS), pp. 1-4 (w/ English translation).

"Basic Oil Analytical Test Methods", 2013 Edition, 2.4.2.2-2013 Fatty Acid Composition (FID Temperature Programmed Gas Chromatography) established by the Japan Oil Chemists' Society (JOCS), pp. 1-4 (w/ English translation).

(Continued)

*Primary Examiner* — Yate' K Cutliff

(74) *Attorney, Agent, or Firm* — Faegre Drinker Biddle & Reath LLP

(57) ABSTRACT

The present disclosure is: a free polyunsaturated fatty acid-containing composition, which comprises at least one free polyunsaturated fatty acid having 20 or more carbon atoms, the content being at least 80.0% of the fatty acids in the composition, and satisfies at least one selected from a group consisting of conditions (1) and (2): (1) the content of conjugated unsaturated fatty acid is 1.0% or less of the fatty acids in the composition, and (2) the Gardner color is less than 3+; and a manufacturing method for the free polyunsaturated fatty acid-containing composition comprising the preparation of a raw material composition containing at least one polyunsaturated fatty acid having 20 or more carbon atoms, and hydrolysis of a reaction solution containing the prepared raw material composition, a lower alcohol, water and an alkali catalyst at a temperature of 10° C. or lower.

7 Claims, No Drawings

(56) References Cited

FOREIGN PATENT DOCUMENTS

| WO | WO-2009/020406 A1 | 2/2009 |
| WO | WO-2013/172346 A1 | 11/2013 |
| WO | WO-2015/083806 A1 | 6/2015 |
| WO | WO-2015/083843 A2 | 6/2015 |
| WO | WO-2015/095688 A1 | 6/2015 |

OTHER PUBLICATIONS

"Fatty Acid Composition by GLC," Marine Oils, American Oil Chemists' Society (AOCS) Official Method Ce 1b-89, 5 pages, 1993.

International Search Report dated Nov. 8, 2016 for PCT/JP2016/075444.

International Search Report and Written Opinion dated Nov. 8, 2016 for PCT/JP2016/075444 [Japanese language].

"Color (Gardner Method)", 3.2.1.1 of the Standard Methods for the Analysis of Fats, Oils, and Related Materials, 2013 Edition, established by Japan Oil Chemists' Society (JOCS), 1 page.

"P-Anisidine Value", 2.5.3 of the Standard Methods for the Analysis of Fats, Oils, and Related Materials, 2013 Edition, established by Japan Oil Chemists' Society (JOCS), 3 pages.

"Conjugated Unsaturated Fatty Acids (Spectrum Method)", Reference 1.14-2013 of the Standard Methods for the Analysis of Fats, Oils, and Related Materials, 2013 Edition, established by Japan Oil Chemists' Society (JOCS), 2 pages.

English Translation of the Written Opinion dated Nov. 8, 2016 for PCT/JP2016/075444.

English Translation of International Preliminary Report on Patentability dated Mar. 6, 2018 for PCT/JP2016/075444.

International Search Report for PCT/JP2016/075445, dated Nov. 15, 2016.

International Search Report and Written Opinion for PCT/JP2016/075445, dated Nov. 15, 2016 [Japanese language].

English Translation of Written Opinion for PCT/JP2016/075445, dated Nov. 15, 2016.

English Translation of International Preliminary Report on Patentability for PCT/JP2016/075445, dated Mar. 6, 2018.

Extended European search report dated Mar. 15, 2019 for EP 16841891.1.

Canadian Office Action dated Mar. 11, 2019 issued in Canadian patent application No. 2,997,052.

Extended European search report dated Apr. 3, 2019 for EP 16841890.3.

Stamenković et al., "Kinetics of sunflower oil methanolysis at low temperatures", Bioresource Technology, Elsevier, Amsterdam, NL, vol. 99, No. 5, Dec. 15, 2007, pp. 1131-1140.

Database CA Accession No. 195455107.

Miklos et al., "Water and Fat Mobility in Myofibrillar Protein gels Explored by Low-Field NMR", Food Biophysics, vol. 10, No. 3, Mar. 11, 2015, pp. 316-323.

Examination report No. 2 dated Jul. 23, 2019 issued in Australian patent application No. 2016317523.

\* cited by examiner

FREE POLYUNSATURATED FATTY ACID-CONTAINING COMPOSITION AND MANUFACTURING METHOD THEREFOR

CROSS REFERENCE TO RELATED APPLICATIONS

This is a continuation application of International Patent Application No. PCT/JP2016/075444 filed Aug. 31, 2016, which claims the benefit of Japanese Patent Application No. 2015-170856, the full contents of all of which are hereby incorporated by reference in their entirety.

BACKGROUND

Technical Field

The present disclosure relates to a free polyunsaturated fatty acid-containing composition and a manufacturing method therefor.

Description of the Related Art

Long-chain polyunsaturated fatty acids having 20 or more carbons, such as eicosadienoic acid, dihomo-γ-linolenic acid (DGLA), eicosatetraenoic acid, arachidonic acid (ARA), eicosapentaenoic acid (EPA), docosatetraenoic acid, docosapentaenoic acid, and docosahexaenoic acid (DHA), have been known to exhibit various functionalities in organisms. Therefore, use of polyunsaturated fatty acids as functional components in products such as medicaments, health food, and cosmetics has been studied. Accordingly, there has been a demand for the production of polyunsaturated fatty acids in large quantities at high concentrations.

In many cases in natural, polyunsaturated fatty acids are present in oils as constituent fatty acids of triacylglycerol (glyceride). Therefore, to obtain a free polyunsaturated fatty acid, hydrolysis of a constituent fatty acid in triacylglycerol or a fatty acid alkyl ester is typically performed.

For example, WO 2013/172346 discloses that a (free) polyunsaturated fatty acid is obtained by hydrolyzing an ester of polyunsaturated fatty acid obtained by a combination of rectification and column chromatography.

WO 2015/083843 discloses that a free fatty acid of DGLA is obtained by hydrolyzing a DGLA lower alkyl ester, which is obtained by producing a lower alkyl ester of a microbial oil and then rectifying using an alkali catalyst to enhance purity.

SUMMARY

In hydrolysis treatment to obtain a free fatty acid, a substance that is not present or that is present in a small amount in the raw material before the treatment may be generated or increased, in addition to the target free polyunsaturated fatty acid. Such a substance is an impurity that is not the target substance, and often has an unidentified structure or function. Therefore, it is desired that the content thereof is made as small as possible in the free polyunsaturated fatty acid-containing composition.

Furthermore, to sufficiently exhibit functions of a free polyunsaturated fatty acid, a composition containing high concentration of the free polyunsaturated fatty acid has been desired, and the concentration of a free polyunsaturated fatty acid has been increased by concentration treatment or the like. The impurities described above may include impurities that are difficult to be removed by following processes due to similarity in structure with the target free polyunsaturated fatty acid or the like. In this case, it is concerned that the concentration of impurities may also increase as the target free polyunsaturated fatty acid is concentrated. It is also considered that precision of the refining is enhanced to remove impurities; however, a limit exists for enhancing precision, and it is industrially disadvantageous from the perspective of treatment efficiency, treatment time, and the like.

Therefore, demands exist for free polyunsaturated fatty acid compositions having less impurities and manufacturing methods for a free polyunsaturated fatty acid composition having less impurities.

The present disclosure includes the following aspects:

[1] A free polyunsaturated fatty acid-containing composition, containing at least one free polyunsaturated fatty acid having 20 or more carbons in an amount that a content thereof is 80.0% or greater of fatty acids in the composition, and the free polyunsaturated fatty acid-containing composition satisfies at least one selected from the group consisting of conditions (1) and (2):

(1) a content of a conjugated unsaturated fatty acid being 1.0% or less of the fatty acids in the composition; and (2) the Gardner color being less than 3+.

[2] The free polyunsaturated fatty acid-containing composition according to [1], where an anisidine value is 5.0 or less.

[3] The free polyunsaturated fatty acid-containing composition according to [1] or [2], where a content of the fatty acid alkyl ester is 0.2% or less of the fatty acids in the composition.

[4] The free polyunsaturated fatty acid-containing composition according to any one of [1] to [3], where the content of the conjugated unsaturated fatty acid is from 0.001% to 1.0% of the fatty acids in the composition.

[5] The free polyunsaturated fatty acid-containing composition according to any one of [1] to [4], where the polyunsaturated fatty acid is at least one selected from the group consisting of eicosadienoic acid, dihomo-γ-linolenic acid, Mead acid, eicosatetraenoic acid, arachidonic acid, eicosapentaenoic acid, docosatetraenoic acid, docosapentaenoic acid, and docosahexaenoic acid.

[6] The free polyunsaturated fatty acid-containing composition according to any one of [1] to [5], where a total content of a residual organic solvent in the composition is 5000 ppm or less.

[7] The free polyunsaturated fatty acid-containing composition according to any one of [1] to [6], where a content of a di- or higher-valent polyunsaturated fatty acid having 18 carbons in the composition is 2.0% or less of the fatty acids in the composition.

[8] A manufacturing method of a free polyunsaturated fatty acid-containing composition, the method including:

providing a raw material composition containing at least one polyunsaturated fatty acid having 20 or more carbons; and performing hydrolysis treatment on a reaction solution containing the provided raw material composition, a lower alcohol, water, and an alkali catalyst in a temperature condition at 10° C. or lower.

[9] The manufacturing method according to [8], where the polyunsaturated fatty acid in the raw material composition is a polyunsaturated fatty acid alkyl ester.

[10] The manufacturing method according to [8] or [9], the method further including adding an acid in a reaction solution after the hydrolysis treatment to terminate the hydrolysis reaction, a pH of the reaction solution after the acid addition being from pH 1.0 to 6.0.

[11] The manufacturing method according to any one of [8] to [10], where an amount of the lower alcohol in the reaction solution is from 0.9 equivalents to 32.0 equivalents relative to an amount of the fatty acids in the raw material composition.

[12] The manufacturing method according to any one of [8] to [111], where an amount of the lower alcohol in the reaction solution is from 0.20 to 8.20 in terms of weight content ratio relative to the water.

[13] The manufacturing method according to any one of [8] to [12], where an amount of the water in the reaction solution is from 6.0 equivalents to 13.0 equivalents relative to the fatty acids in the raw material composition.

[14] The manufacturing method according to any one of [8] to [13], where an amount of the alkali catalyst in the reaction solution is from 1.0 equivalent to 2.3 equivalents relative to the fatty acids in the raw material composition.

[15] The manufacturing method according to any one of [8] to [14], where the alkali catalyst is at least one selected from the group consisting of sodium hydroxide and potassium hydroxide.

[16] The manufacturing method according to any one of [8] to [15], where the temperature condition of the hydrolysis treatment is from −20° C. to 10° C.

[17] The manufacturing method according to any one of [8] to [16], where the raw material composition is derived from a microbial raw material.

[18] A food product, supplement, medicament, cosmetic, or animal feed containing the free polyunsaturated fatty acid-containing composition described in any one of [1] to [7].

[19] Use of the free polyunsaturated fatty acid-containing composition described in any one of [1] to [7] in a manufacturing method of a food product, supplement, medicament, cosmetic, or animal feed.

According to aspects of the present disclosure, a free polyunsaturated fatty acid composition having less impurities and a manufacturing method for a free polyunsaturated fatty acid composition having less impurities can be provided.

DETAILED DESCRIPTION

The free polyunsaturated fatty acid-containing composition according to an aspect of the present disclosure is a free polyunsaturated fatty acid-containing composition containing at least one free polyunsaturated fatty acid having 20 or more carbons in an amount that a content thereof is 80.0% or greater of fatty acids in the composition, and the free polyunsaturated fatty acid-containing composition satisfies at least one selected from the group consisting of conditions (1) and (2):

(1) a content of a conjugated unsaturated fatty acid being 1.0% or less of the fatty acids in the composition; and (2) the Gardner color being less than 3+.

The manufacturing method of a free polyunsaturated fatty acid according to an aspect of the present disclosure is a manufacturing method of a free polyunsaturated fatty acid-containing composition, the method including:

providing a raw material composition containing at least one polyunsaturated fatty acid having 20 or more carbons; and performing hydrolysis treatment on a reaction solution containing the provided raw material composition, a lower alcohol, water, and an alkali catalyst in a temperature condition at 10° C. or lower.

A composition containing a free long-chain polyunsaturated fatty acid having 20 or more carbons has higher polarity compared to the polarity of a long-chain polyunsaturated fatty acid in an alkyl ester form or glyceride form and may exhibit different behavior from the behavior of the alkyl ester form or the glyceride form. In particular, conjugated unsaturated fatty acid or a coloring substance may be increased as an impurity during a hydrolysis step by an alkali catalyst to obtain a free polyunsaturated fatty acid in high concentration. It was found that, unlike the case of a composition containing a long-chain polyunsaturated fatty acid in an alkyl ester form or glyceride form, these impurities are difficult to separate or to be removed from the composition containing a free long-chain polyunsaturated fatty acid in high concentration. Meanwhile, it was also found that these impurities are generated or increased due to heat in the hydrolysis step, and generation or increase in these substances can be suppressed by setting the temperature condition of the hydrolysis step to a particular range.

That is, in the free polyunsaturated fatty acid-containing composition, at least one of the content of the conjugated unsaturated fatty acid or the content of the coloring substance is lower than the content of the case where the hydrolysis treatment with an alkali catalyst to obtain a free fatty acid is performed at a conventional temperature condition. It was unexpected that each of the content of the conjugated unsaturated fatty acid and the content of the coloring substance can be adjusted by setting the temperature condition in the hydrolysis treatment to obtain a fatty acid in a free form to a specific range, and can be reduced compared to each content before the hydrolysis treatment. For example, the content of at least one selected from the group consisting of the conjugated unsaturated fatty acid and the coloring substance, which is increased when the temperature condition of typical hydrolysis treatment using an alkali catalyst, such as 70° C., is applied, can be reduced by lowering the temperature condition of the hydrolysis treatment to a specific range.

Accordingly, the content of the conjugated unsaturated fatty acid and/or the coloring substance that is generated or increased in the hydrolysis step is small as well as the content of at least one of free polyunsaturated fatty acid having 20 or more carbons, which is the target, is high, in this free polyunsaturated fatty acid-containing composition. Therefore, the content of these particular impurities is small, and better function of the at least one of free polyunsaturated fatty acid having 20 or more carbons, which is the target, can be favorably exhibited.

The manufacturing method of this free polyunsaturated fatty acid-containing composition includes performing the hydrolysis treatment on the raw material composition in a temperature condition of 10° C. or lower. As a result, the content of the particular impurities described above is small, and the composition containing at least one free polyunsaturated fatty acid having 20 or more carbons, which is the target, can be efficiently obtained.

The terms "oil" and "oil and fat" in the present specification include oils containing only triglycerides, and also include crude oils containing triglycerides as a main component and other lipids such as diglycerides, monoglycerides, phospholipids, cholesterol, and free fatty acids. "Oil" and "oil and fat" mean compositions containing these lipids.

The term "fatty acid" not only indicates a free saturated or unsaturated fatty acid itself, but also includes fatty acids contained as constituent units in free saturated or unsaturated fatty acid alkyl esters, triglycerides, diglycerides, monoglycerides, phospholipids, steryl esters, and the like, which can also be called constituent fatty acids. In the present specification, unless otherwise noted or indicated, when a fatty acid that is present or used is mentioned, presence or use of fatty acid-containing compounds in any form is included. Examples of forms of compounds containing fatty acids include a free fatty acid form, a fatty acid alkyl ester form, a glyceryl ester form, a phospholipid form, and a steryl ester form. When a fatty acid is specified, one form may be present, or a mixture of two or more forms may be present.

It has been empirically determined that the reaction efficiency of hydrolysis of fatty acids is high, and after hydrolysis, a composition containing mainly fatty acid in a form of free fatty acids is obtained. For this reason, unless otherwise specified, fatty acids after the processing step may be denoted while omitting that they are a composition or that the fatty acid is of a free fatty acid form. However, this does not completely negate the fact that fatty acids in a form other than a free fatty acid form are included.

It has been empirically determined that the reaction efficiency of alcoholysis of oils and fats or fatty acid esters is high, and after alcoholysis, a composition containing mainly fatty acid in a fatty acid alkyl ester form is obtained. For this reason, unless otherwise specified, fatty acids after the processing step are denoted while omitting that they are a composition or that the fatty acid is in an alkyl ester form. However, this does not completely negate the fact that fatty acids in a form other than an alkyl ester form are included.

When denoting fatty acids, a numerical expression may be used, whereby the number of carbons, the number of double bonds, and the locations of double bonds are each expressed in a simplified manner using numbers and alphabets, respectively. For example, a saturated fatty acid having 20 carbons is denoted as "C20:0". A monounsaturated fatty acid having 18 carbons is denoted as "C18:1" or the like. Dihomo-γ-linolenic acid is denoted as "C20:3, n-6" or the like. Note that "n-6" is denoted also as ω-6, and this indicates that the bonding position of a first double bond is at the sixth position when the position is counted from the last carbon (ω) to the carboxy group. This method is known to those of ordinary skill in the art, and those of ordinary skill in the art can easily specify fatty acids expressed in accordance with this method.

In the present specification, the term "crude oil" means a mixture of the lipids described above, and means an oil in the state obtained by extraction from an organism. In the present specification, the term "refined oil" means an oil from which substances, such as phospholipids and cholesterol, other than the target substance which have been removed by performing at least one oil and fat refining process selected from the group consisting of a degumming process, a deacidification process, a decoloring process, and a deodorizing process.

In the present specification, in addition to an independent step, the term "step" also refers to a step that achieves an intended object of the step even when the step cannot be clearly distinguished from other steps.

In the present specification, numeric ranges indicated by "to" are ranges that include the minimum and maximum values each stated before and after the "to." In the present specification, the terms "not greater than" and "less than" in regard to percentages mean ranges including 0%, which is the case of "not contained", or a value undetectable by present means, unless the lower limit is specifically stated.

In the present specification, in a case where multiple substances corresponding to each of the components in the composition are present, the amount of each component in the composition, unless otherwise noted, is taken to mean the total amount of these multiple substances present in the composition. In the present specification, in the case where multiple substances corresponding to each of the components in the composition are present, the content of each component in the composition, unless otherwise noted, is taken to mean the total content of these multiple substances present in the composition.

In the present specification, unless otherwise noted, when a numerical range that only specifies one or a plurality of upper limit values and a numerical range that only specifies one or a plurality of lower limit values are described for an identical target, an embodiment of the present disclosure includes a numerical range having a combination of any upper limit value that is chosen from the one or the plurality of the upper limit values and any lower limit value that is chosen from the one or the plurality of the lower limit values.

The content of the fatty acids in the composition of the present specification is determined based on the fatty acid composition unless otherwise noted. The composition of fatty acids may be determined by a normal method. Specifically, when the fatty acids in the composition to be measured are substances other than fatty acid lower alkyl esters, fatty acid lower alkyl esters, which is obtained by subjecting the fatty acids to be measured to esterification by using a lower alcohol and a catalyst, are used. When the fatty acids in the composition to be measured are fatty acid lower alkyl esters, the fatty acids to be measured are used as is. Thereafter, the obtained fatty acid lower alkyl esters are analyzed as a sample using gas chromatography. Peaks corresponding to each of the fatty acids are identified in the obtained gas chromatography chart, and the peak area of each of the fatty acids is determined using the Agilent ChemStation integration algorithm (revision C.01.03[37], Agilent Technologies). "Peak area" indicates a ratio (area percent) of the peak area for respective components to the area of all peaks as determined in charts analyzed by gas chromatography, thin-layer chromatography/flame ionization detector (TLC/FID) or the like of oil and fat having various fatty acids as constituent components, and indicates the content ratio of the component of the peak. The value according to the area percent obtained by the measurement method described above is the same as the value according to the weight percent of each fatty acid relative to the total weight of the fatty acids in a sample, and may be used interchangeably. Refer to "Basic Oil Analytical Test Methods", 2013 Edition, 2.4.2.1-2013 Fatty Acid Composition (FID constant temperature gas chromatograph method) and 2.4.2.2-2013 Fatty Acid Composition (FID heating gas chromatograph method) established by the Japan Oil Chemists' Society (JOCS).

The fatty acid composition was determined by gas chromatography by the method indicated in the examples. Detailed conditions are indicated in examples.

Free Polyunsaturated Fatty Acid-Containing Composition

The free polyunsaturated fatty acid-containing composition according to an embodiment of the present disclosure is a free polyunsaturated fatty acid-containing composition containing at least one free polyunsaturated fatty acid having 20 or more carbons in an amount that a content thereof is 80.0% or greater of fatty acids in the composition, and the free polyunsaturated fatty acid-containing composition satisfies at least one selected from the group consisting of conditions (1) and (2) below:

(1) the content of a conjugated unsaturated fatty acid being 1.0% or less of the fatty acids in the composition: and (2) the Gardner color being less than 3+.

The free polyunsaturated fatty acid-containing composition satisfies at least one selected from the group consisting of the conditions (1) and (2) and contains at least 80.0% of at least one free polyunsaturated fatty acid having 20 or more carbons. As a result, the amount of particular impurities is small, and better functions of the at least one free polyunsaturated fatty acid having 20 or more carbons can be favorably exhibited.

In the present specification, unless otherwise noted, the free polyunsaturated fatty acid having 20 or more carbons may be referred to as "free LC-PUFA". In the present specification, the free polyunsaturated fatty acid-containing composition according to an embodiment of the present disclosure may be simply referred to as "free LC-PUFA-containing composition".

The polyunsaturated fatty acid having 20 or more carbons in the free LC-PUFA-containing composition includes di- or higher valent unsaturated fatty acids and, preferably, tri- or higher valent unsaturated fatty acids. The number of carbon atoms of the polyunsaturated fatty acid refers to the number of carbon atoms of the constituent fatty acids. Examples of polyunsaturated fatty acid having 20 or more carbons include polyunsaturated fatty acids having from 20 to 22 carbons. Specific examples thereof include eicosadienoic acid (C20:2, n-9, EDA), dihomo-γ-linolenic acid (C20:3, n-6, DGLA), Mead acid (C20:3, n-9, MA), eicosatetraenoic acid (C20:4, n-3, ETA), arachidonic acid (C20:4, n-6, ARA), eicosapentaenoic acid (C20:5, n-3, EPA), docosatetraenoic acid (C22:4, n-6, DTA), docosapentaenoic acid (C22:5, n-3, $_{n-3}$DPA), docosapentaenoic acid (C22:5, n-6, $_{n-6}$DPA), and docosahexaenoic acid (C22:6, n-3, DHA). The free LC-PUFA-containing composition needs to contain at least one of these polyunsaturated fatty acids and may contain a combination of two or more of these. Examples of the LC-PUFA having a combination of two or more of these include a combination of DGLA and EPA, a combination of DGLA and $_{n-3}$DPA, a combination of DGLA and DHA, a combination of ARA and EPA, a combination of ARA and $_{n-3}$DPA, a combination of ARA and DHA, a combination of EPA and $_{n-3}$DPA, a combination of DHA and $_{n-3}$DPA, a combination of DHA and EPA, and a combination of EPA and DHA and $_{n-3}$DPA.

The free LC-PUFA-containing composition contains one selected from the polyunsaturated fatty acids described above and may contain no other polyunsaturated fatty acids, or does not need to contain other particular one or two or more polyunsaturated fatty acids described above as long as the free LC-PUFA-containing composition contains at least one polyunsaturated fatty acid having from 20 to 22 carbons described above as LC-PUFA. For example, the free LC-PUFA-containing composition may be prepared so as to not contain at least one type selected from the group consisting of eicosadienoic acid (C20:2, n-9), dihomo-γ-linolenic acid (C20:3, n-6), Mead acid (C20:3, n-9), eicosatetraenoic acid (C20:4, n-3), arachidonic acid (C20:4, n-6), eicosapentaenoic acid (C20:5, n-3), docosatetraenoic acid (C22:4, n-6), docosapentaenoic acid (C22:5, n-3), docosapentaenoic acid (C22:5, n-6), and docosahexaenoic acid (C22:6, n-3). Here, "not containing polyunsaturated fatty acids" means that the content of the target polyunsaturated fatty acid is less than 5% or 0% of the fatty acids in the composition.

The content of the LC-PUFA in the free LC-PUFA-containing composition is 80.0% or greater of the fatty acids in the composition. Because the free LC-PUFA-containing composition containing 80.0% or greater of the LC-PUFA can exhibit superior functions of LC-PUFA. The lower limit value of the content of the target LC-PUFA in the free LC-PUFA-containing composition may be 85.0%, 90.0%, 95.0%, 97.0%, 98.0%, 99.0%, or 99.5% of the fatty acids in the composition. When the content of the LC-PUFA is higher, superior functions of the LC-PUFA can be exhibited. The upper limit value of the content of the LC-PUFA is not particularly limited and, for example, the upper limit value may be 99.9% or 98.0%. The content of the LC-PUFA in the present composition may be in a range of any combination of a chosen value of the upper limit value and a chosen value of the lower limit value described above. For example, the content may be from 80.0% to 99.9%, from 90.0% to 99.9%, from 90.0% to 98%, from 95.0% to 99.9%, from 97.0% to 99.9%, or from 97.0% to 98.0% of the fatty acids in the composition.

The free LC-PUFA-containing composition satisfies at least one selected from the group consisting of the conditions (1) and (2).

The condition (1) that may be satisfied by the free LC-PUFA-containing composition relates to the content of the conjugated unsaturated fatty acid. The content of the conjugated unsaturated fatty acid is 1.0% or less of the fatty acids in the composition. Although the conjugated unsaturated fatty acid differs depending on the type of the fatty acid and the type of the LC-PUFA in the raw material composition used for the hydrolysis treatment, examples of the conjugated unsaturated fatty acid include conjugated dienoic acid, conjugated trienoic acid, and conjugated tetraenoic acid. The conjugated unsaturated fatty acid can be quantified based on the absorbance of the target conjugated unsaturated fatty acid. The content of the conjugated unsaturated fatty acid in the free LC-PUFA-containing composition is a content of the conjugated unsaturated fatty acid obtained by measuring ultraviolet spectrum of a sample and calculating using a stipulated calculation formula, and is a value measured in accordance with the conjugated unsaturated fatty acid (spectrum method) stipulated in Reference 1.14 of Standard Methods for the Analysis of Fats, Oils, and Related Materials, 2013 Edition, established by Japan Oil Chemists' Society (JOCS). When the composition in the sample contains a component other than the fatty acids, the amount of the conjugated unsaturated fatty acid can be determined based on the amount of the fatty acids in the composition.

The content of the conjugated unsaturated fatty acid in the free LC-PUFA-containing composition may be 0.8% or less, 0.7% or less, 0.6% or less, 0.5% or less, 0.4% or less, or 0.3% or less, of the fatty acids in the composition. A smaller content of the conjugated unsaturated fatty acid tends to exhibit superior oxidation stability of the composition. The lower limit value of the content of the conjugated unsaturated fatty acid may be 0.1%, 0.2%, 0.01%, or 0.001%. For example, the content of the conjugated unsaturated fatty acid of the free LC-PUFA-containing composition may be from 0.001% to 1.0%, from 0.01% to 0.8%, from 0.1% to 0.7%, or from 0.2% to 0.7%, of the fatty acids in the composition.

The condition (2) that may be satisfied by the free LC-PUFA-containing composition relates to the Gardner color and is the Gardner color of less than 3+. The Gardner color is an indicator varied based on the content of the coloring substance present in the free LC-PUFA-containing composition and indicates that the degree of coloration of the composition is increased in the following order: 1−, 1, 1+, 2−, 2.2+. 3−, 3.3+. 4−, 4, 4+, 5−, 5, 5+. Satisfying the condition (2) means that the color of the free LC-PUFA-containing composition is the Gardner color of less than 3+, that is, the color corresponds to any one of 1−, 1, 1+, 2−, 2, 2+, 3−, or 3. The Gardner color is determined based on 3.2.1.1 of the Standard Methods for the Analysis of Fats, Oils, and Related Materials, 2013 Edition, established by Japan Oil Chemists' Society (JOCS).

The Gardner color of the free LC-PUFA-containing composition may be 3− or less, 2+ or less, 2 or less, 1+ or less, or 1−. The free LC-PUFA-containing composition exhibiting a lower value of the Gardner color has a smaller amount of the coloring substance that may be generated due to hydrolysis using an alkali catalyst and tends to facilitate quality control and tends to provide a wider selection for commercialization.

The free LC-PUFA-containing composition can satisfy one of the condition (1) or (2). That is, when the free LC-PUFA-containing composition satisfies the condition (1), the Gardner color may be 3+ or greater, and in this case, for example, the Gardner color may be 4 or less or 4− or less. When the free LC-PUFA-containing composition satisfies the condition (2), the content of the conjugated unsaturated fatty acid may be greater than 1.0%, and in this case, for example, the content may be 3.0% or less, 2.5% or less, 2.0% or less, or 1.5% or less.

In the free LC-PUFA-containing composition, the condition (3) may be an anisidine value (AnV) of 5.0 or less, 4.5 or less, 4.0 or less, 3.5 or less, 3.0 or less, or 2.5 or less. The anisidine value is an indicator varied based on the content of the oxidized substance present in the free LC-PUFA-containing composition. The free LC-PUFA-containing composition showing a lower anisidine value has a smaller content of the oxidized substance. The anisidine value is determined based on 2.5.3 of the Standard Methods for the Analysis of Fats, Oils, and Related Materials, 2013 Edition, established by Japan Oil Chemists' Society (JOCS).

There can be cases where the free LC-PUFA-containing composition only satisfies the condition (1), where the free LC-PUFA-containing composition only satisfies the condition (2), or where the free LC-PUFA-containing composition satisfies the conditions (1) and (2). Furthermore, in addition to these, the condition (3) may be satisfied. The free LC-PUFA-containing composition includes the following, for example:

(a) a free LC-PUFA-containing composition having the content of the conjugated unsaturated fatty acid of 1.0% or less of the fatty acids in the composition and having the Gardner color of 3+ or greater;

(b) a free LC-PUFA-containing composition having the content of the conjugated unsaturated fatty acid of greater than 1.0% of the fatty acids in the composition and having the Gardner color of 3 or less;

(c) a free LC-PUFA-containing composition having the content of the conjugated unsaturated fatty acid of 1.0% or less of the fatty acids in the composition and having the Gardner color of 3 or less;

(d) a free LC-PUFA-containing composition having the content of the conjugated unsaturated fatty acid of 1.0% or less of the fatty acids in the composition, having the Gardner color of 3+ or greater, and having the anisidine value of 5.0 or less;

(e) a free LC-PUFA-containing composition having the content of the conjugated unsaturated fatty acid of greater than 1.0% of the fatty acids in the composition, having the Gardner color of 3 or less, and having the anisidine value of 5.0 or less: and (f) a free LC-PUFA-containing composition having the content of the conjugated unsaturated fatty acid of 1.0% or less of the fatty acids in the composition, having the Gardner color of less than 3+, and having the anisidine value of 5.0 or less.

In the free LC-PUFA-containing compositions of (a) to (c) described above, the anisidine value may be greater than 5.0 and may be 6.0 or less, or 5.5 or less. In the free LC-PUFA-containing compositions of (a) and (d) described above, the Gardner color may be 3+ or greater and may be 6 or less, 5+ or less, 5 or less, 5− or less, 4+ or less, 4 or less, or 4− or less. In the free LC-PUFA-containing compositions of (b) and (e) described above, the content of the conjugated unsaturated fatty acid may be 2.5% or less, 2.0% or less, or 1.5% or less.

The free LC-PUFA-containing composition of (f) described above includes the following, for example:

(f1) a free LC-PUFA-containing composition having the content of the conjugated unsaturated fatty acid of 0.7% or less, having the Gardner color of 2+ or less, and having the anisidine value of 5.0 or less;

(f2) a free LC-PUFA-containing composition having the content of the conjugated unsaturated fatty acid of 0.7% or less, having the Gardner color of less than 3+, and having the anisidine value of 4.0 or less;

(f3) a free LC-PUFA-containing composition having the content of the conjugated unsaturated fatty acid of 0.7% or less, having the Gardner color of 2+ or less, and having the anisidine value of 4.0 or less;

(f4) a free LC-PUFA-containing composition having the content of the conjugated unsaturated fatty acid of 0.4% or less, having the Gardner color of 1+ or less, and having the anisidine value of 3.5 or less;

(f5) a free LC-PUFA-containing composition having the content of the conjugated unsaturated fatty acid of 0.4% or less, having the Gardner color of 1 or less, and having the anisidine value of 2.5 or less; and (f6) a free LC-PUFA-containing composition having the content of the conjugated unsaturated fatty acid of 0.3% or less, having the Gardner color of 1−, and having the anisidine value of 3.5 or less.

In the free LC-PUFA-containing compositions of (a) to (f) described above, the content of the conjugated unsaturated fatty acid may be 0.001% or greater, 0.01% or greater, or 0.1% or greater.

The free LC-PUFA-containing composition may have a small content of the fatty acid alkyl ester. In the step of producing a free fatty acid, the fatty acid alkyl ester may be a raw material substance of alkaline hydrolysis or may be a product that can be produced from the free fatty acid through a reverse reaction. The free LC-PUFA-containing composition having a smaller content of the fatty acid alkyl ester can have a higher content of the free LC-PUFA and tends to exhibit superior bioabsorbability, especially superior intestinal absorbability, of the composition. The content of the fatty acid alkyl ester of the free LC-PUFA-containing composition may be 0.2% or less, 0.1% or less, 0.05% or less, 0.04% or less, 0.03% or less, 0.02% or less, or 0.01% or less, of the fatty acids in the composition. The lower limit value of the content of the fatty acid alkyl ester is not particularly limited, and for example, the lower limit value may be 0.0005%. When the content of the fatty acid alkyl ester is 0.0005% or greater, the composition is less likely to crystallize, and the flowability tends to be enhanced.

The free LC-PUFA-containing composition may be a free LC-PUFA-containing composition having a smaller content of fatty acids other than the LC-PUFA. When the content of the fatty acids other than the LC-PUFA in the composition is low, exhibition of functions is expected in a degree corresponding to the content of the LC-PUFA, and also effect due to other fatty acids other than the LC-PUFA can be suppressed. Examples of other fatty acids that can reduce the content thereof in the free LC-PUFA-containing composition include saturated or unsaturated fatty acids having less than 20 carbons, and saturated fatty acids having 22 or more carbons. Specific examples of the saturated or unsaturated fatty acid having less than 20 carbons include saturated fatty acids having 18 carbons, monounsaturated fatty acids having 18 carbons, divalent unsaturated fatty acids having 18 carbons, trivalent unsaturated fatty acids having 18 carbons, and tetravalent unsaturated fatty acids having 18 carbons. Examples of the saturated fatty acid having 22 or more carbons include saturated fatty acids having 22 carbons and saturated fatty acids having 24 carbons.

Among these fatty acids other than the LC-PUFA, the free LC-PUFA-containing composition may be a free LC-PUFA-containing composition having a low content of a di- or higher-valent polyunsaturated fatty acid having 18 carbons. For example, the content of the di- or higher-valent polyunsaturated fatty acid having 18 carbons may be 2.0% or less, 1.5% or less, 1.0% or less, or 0.8% or less, of the fatty acids in the composition. The lower limit value of the content of the fatty acids other than the LC-PUFA may be, for example, 0.001% or greater, 0.005% or greater, or 0.01%. The content of the di- or higher-valent polyunsaturated fatty acid having 18 carbons may be, for example, from 0.001% to 2.0%, from 0.005% to 1.5%, from 0.01% to 1.5%, or from 0.01% to 1.0%.

The free LC-PUFA-containing composition may contain a fatty acid in a form other than the fatty acids described above. Examples of the fatty acids in other forms include triglyceride, diglyceride, monoglyceride, phospholipid, and steryl esters. The content of the fatty acids in other forms needs to be an amount that corresponds to the rest of the free LC-PUFA-containing composition excluding the LC-PUFA. The content may be less than 20.0%, less than 10.0%, less than 5.0%, less than 2.0%, less than 1.0%, or less than 0.5%, of the fatty acids in the composition.

The content of the fatty acids in the free LC-PUFA-containing composition may be 97.0 wt. % or greater, 98.0 wt. % or greater, 99.0 wt. % or greater, 99.5 wt. % or greater, or 100 wt. %, of the total weight of the composition. The content of the fatty acids in the free LC-PUFA-containing composition can be confirmed by a publicly known technique, such as TLC/FID. The free LC-PUFA-containing composition may contain a component other than the fatty acids. Examples of such other component that may be contained in the free LC-PUFA-containing composition include antioxidants, such as tocopherol, vitamin C, and vitamin C derivatives, and solvents, such as ethanol.

The free LC-PUFA-containing composition may be produced by any manufacturing method as long as the free LC-PUFA-containing composition has characteristics described in the present specification, and preferably is a free LC-PUFA-containing composition produced by the manufacturing method described below.

Manufacturing Method

The manufacturing method of the free LC-PUFA-containing composition in an embodiment of the present disclosure includes: providing a raw material composition containing at least one polyunsaturated fatty acid having 20 or more carbons; and performing hydrolysis treatment on a reaction solution containing the provided raw material composition, a lower alcohol, water, and an alkali catalyst in a temperature condition at 10° C. or lower: and, as necessary, other step(s). According to the present manufacturing method, a free LC-PUFA-containing composition having a lower content of the conjugated unsaturated fatty acid and/or the coloring substance than the content of the case where hydrolysis treatment is performed at a temperature of higher than 10° C. can be efficiently obtained.

In the step of providing the raw material composition, a raw material composition that had been acquired may be provided or a raw material composition that had been separately produced may be provided as long as the raw material composition contains at least one LC-PUFA. The raw material composition may be a raw material composition derived from an organism, such as a raw material composition derived from a marine raw material, a raw material composition derived from a microbial raw material, a raw material composition derived from a plant raw material, and a raw material composition derived from an animal raw material. The raw material composition may be a composition containing LC-PUFA in a triglyceride form, and may be a composition containing an LC-PUFA alkyl ester. The LC-PUFA alkyl ester-containing composition is preferably obtained by subjecting a bio-oil containing LC-PUFA in a triglyceride form to alkyl esterification.

The bio-oil containing LC-PUFA may be a bio-oil, such as a marine raw material oil derived from fish or the like, a microbial oil derived from microorganisms, and a plant oil derived from plants, and for example, may be a microbial oil. The bio-oil means an oil obtained by using biomass as its origin, and the microbial oil means an oil obtained by using microbial biomass as its origin. The bio-oil may be a bio-oil that originates from genetically modified materials. The term "biomass" means an aggregation or lump of cells at a certain point of time during growth in a certain region or in an ecosystem.

Examples of the marine raw material oil include lipids including oils and fats, phospholipids, wax esters, and the like contained in fish, shellfish, or marine animals. Examples of the marine raw material oil include oils derived from fish such as herring, sardine, anchovy, menhaden, pilchard, saury, tuna, bonito, hake, catfish, capelin, red fish, white fish, mackerel, jack mackerel, yellowtail, sand eel, pout, salmon, pollock, cod, halibut, trout, blue whitening, sprat, shark, and dogfish; oils derived from mollusks such as squid, clam, and abalone: oils derived from crustaceans such as krill; oils derived from animals such as seal, sealion, sea bear, and walrus, and mixtures of these oils.

The microorganism may be a microorganism that produces lipids or a microorganism that can produce lipids, and examples thereof include algae, true fungi, bacteria, fungi, and stramenopiles.

Examples of the algae include the genus *Labyrinthula* (*Labyrinthula mycota*).

Examples of the true fungi include the genus *Yarrowia*, the genus *Candida*, the genus *Saccharomyces*, the genus *Schizosaccharomyces*, and the genus *Pichia*.

Examples of the bacteria include *Agrobacterium, Bacillus, Escherichia, Pseudomonas*, and *Actinomyces*.

Examples of the fungi include at least one type selected from the group consisting of the genus *Mortierella*, the genus *Conidiobolus*, the genus *Phythium*, the genus *Phytophthora*, the genus *Penicillium*, the genus *Cladosporium*, the genus *Mucor*, the genus *Fusarium*, the genus *Aspergillus*, the genus *Rhodotorula*, the genus *Entomophthora*, the genus *Echinosporangium*, and the genus *Saprolegnia*. Of these, microorganisms belonging to the genus *Mortierella* are even more preferable. Examples of the microorganisms belonging to the genus *Mortierella* include microorganisms belonging to the subgenus *Mortierella* such as *Mortierella elongata, Mortierella exigua, Mortierella hygrophila,* and *Mortierella alpina*.

Examples of the plant include plants of the genus *Brassica,* the genus *Helianthus,* the genus *Gossypium,* the genus *Linum,* the genus *Nicotiana,* the genus *Citrus,* the genus *Allium,* the genus *Triticum,* the genus *Hordeum,* the genus *Avena,* the genus *Secale,* the genus *Oryza,* the genus *Saccharum,* the genus *Zea,* the genus *Sorghum* as well as soybean, tomato, potato, pea, frijol, peanut, *Medicago*, celery, paseley, clover, carrot, radish, sugar beet, cucumber, spinach, cassava, olive, apple, banana, melon, grape, strawberry, coconut plant, coffee plant, and pepper.

The raw material oil that is subjected to the alkyl esterification may be a crude oil or a refined oil. The crude oil may be an oil obtained from a marine raw material or may be an oil obtained from a microbial raw material. A refined oil can be obtained by subjecting a crude oil to a de-gumming process, deacidification process, decoloration process using an activated clay or active carbon, washing process, deodorization process by steam distillation or the like, and crude oil refining process that removes substances other than the target, such as phospholipids and sterols.

In the step of performing alkyl esterification, the raw material oil is decomposed into a lower alkyl ester via alcoholysis using a lower alcohol. Examples of the lower alcohol include lower alcohols typically used in alkyl esterification of fatty acids, such as lower alcohols having from 1 to 3 carbons. In the alcoholysis, a lower alcohol such as ethanol and a catalyst or enzyme are added and reacted with a raw material oil to produce an ethyl ester from the fatty acid bonded to glycerin. As the catalyst, an alkali catalyst, an acid catalyst, or the like is used. As the enzyme, lipase is used.

The crude oil or the refined oil, or the fatty acid alkyl ester-containing composition obtained by the alkyl esterification treatment may contain at least one other fatty acid in addition to the target LC-PUFA. One type of method or a combination of two or more types of methods, exemplified by the distillation, rectification, column chromatography, low temperature crystallization method, urea clathrate method, liquid-liquid countercurrent distribution chromatography, or the like, may be used to concentrate or isolate the particular LC-PUFA from the crude oil, the refined oil, or the fatty acid alkyl ester-containing composition. A combination of distillation or rectification, and column chromatography or liquid-liquid countercurrent distribution chromatography is preferably used. When the step of concentrating or isolating the particular LC-PUFA is performed, the content of target LC-PUFA, which may be contained in the final LC-PUFA-containing composition, in the fatty acids is increased and the content of other fatty acid other than the target LC-PUFA in the fatty acids can be reduced.

For example, in a case in which rectification is used, the rectification step is preferably carried out by distillation using a reduced pressure at the top of the distillation column of less than or equal to 10 mmHg (1333 Pa), using a temperature of the column bottom in the range of 165° C. to 210° C., and preferably 170° C. to 195° C., from the perspective of suppressing the denaturation of the fatty acid due to heat, and increasing efficiency of rectification. The pressure at the top of the distillation column is preferably as low as possible, and more preferably lower than or equal to 0.1 mmHg (13.33 Pa). No particular limitation is imposed on the temperature at the top of the column, and for example, this temperature may be set to lower than or equal to 160° C. In the rectification step, a raw material composition having an even higher content of the LC-PUFA, such as LC-PUFA alkyl ester, may be obtained.

Reverse phase distribution type column chromatography is preferred as the column chromatography. The reverse phase column chromatography may be reverse phase column chromatography that is known in the art, and high-performance liquid chromatography (HPLC) using a base material modified with octadecylsilyl groups (ODS) as a stationary phase is particularly preferable.

The composition obtained by the concentration or isolation step is a composition having a high content of the target LC-PUFA and, for example, the content of the target LC-PUFA may be 80.0% or greater, 85.0% or greater, 90.0% or greater, 95.0% or greater, 97.0% or greater, 98.0% or greater, 99.0% or greater, or 99.5% or greater, of the fatty acids. This composition containing a high concentration of LC-PUFA can be used as a raw material composition.

In the step of performing hydrolysis treatment, a reaction solution containing the provided raw material composition, a lower alcohol, water, and an alkali catalyst is subjected to hydrolysis treatment in a temperature condition at 10° C. or lower. In the present specification, this hydrolysis treatment with an alkali catalyst may be referred to as alkali hydrolysis treatment.

The reaction solution used in the alkali hydrolysis treatment contains a raw material composition, a lower alcohol, water, and an alkali catalyst. The raw material composition may be a bio-oil or may be an LC-PUFA alkyl ester-containing composition. The concentration (w/w) of the raw material composition in the reaction solution may be from 10.0 wt. % to 70.0 wt. %, from 20.0 wt. % to 60.0 wt. %, or from 40 wt. % to 50 wt. %, from the perspective of reaction efficiency.

Examples of the lower alcohol include lower alcohols typically used for decomposing bio-oils or fatty acid alkyl esters to obtain free fatty acids, such as lower alcohols having from 1 to 3 carbons. The amount of the lower alcohol in the reaction solution needs to be an amount that is effective in decomposing a fatty acid in the raw material composition into a free fatty acid. For example, the amount may be from 0.9 equivalents to 32.0 equivalents, from 0.92 equivalents to 20.0 equivalents, from 0.95 equivalents to 14 equivalents, from 2.0 equivalents to 10.0 equivalents, from 3.0 equivalents to 7.0 equivalents, or from 4.5 equivalents to 5.5 equivalents, relative to the amount of the fatty acids in the composition. When the ratio of the lower alcohol to the fatty acids in the raw material composition is 0.9 equivalents or greater, the reaction tends to proceed at a more favorable rate, and suppression of generation of the coloring substance tends to be facilitated. On the other hand, when the ratio is 32.0 equivalents or less, the condition after the termination of the reaction tends to be stabilized, and progression of reverse reaction that may generate fatty acid alkyl esters tends to be effectively suppressed. The amount of the lower alcohol in the reaction solution includes both the amount of the lower alcohol added during the preparation of the reaction solution and the amount of the lower alcohol that is produced during the reaction as a byproduct in the reaction solution. In the present specification, "equivalent" refers to "molar equivalent". This is the same hereafter.

The amount of the lower alcohol in the reaction solution may be from 0.20 to 8.20, from 0.23 to 4.50, from 0.25 to 3.50, from 0.60 to 2.50, or from 1.20 to 1.50, in terms of weight ratio relative to the amount of water. When the weight ratio of lower alcohol to water is in this range, the alkali hydrolysis proceeds even more favorably, the condition after the termination of the reaction tends to be stabilized, and progression of reverse reaction that may generate fatty acid alkyl esters tends to be effectively suppressed. The amount of the lower alcohol in the reaction solution includes both the amount of the lower alcohol added during the preparation of the reaction solution and the amount of the lower alcohol that is produced during the reaction as a byproduct in the reaction solution.

The amount of the reaction solution in water may be from 6.0 equivalents to 13.0 equivalents, from 7.0 equivalents to 12.0 equivalents, from 8.0 equivalents to 11.0 equivalents, or from 9.0 equivalents to 10.0 equivalents, relative to the amount of the fatty acids in the raw material composition. When the weight ratio of water to raw material composition is in this range, the alkali hydrolysis can be more favorably proceeded.

The alkali catalyst used in the alkali hydrolysis treatment may be an alkali metal hydroxide, may be sodium hydroxide, potassium hydroxide, or the like, may be at least one selected from the group consisting of sodium hydroxide and potassium hydroxide, and is more preferably sodium hydroxide. The amount of the alkali catalyst used in the alkali hydrolysis treatment needs to be in a range that can produce a free fatty acid from the raw material composition. For example, the amount may be from 1.0 equivalent to 2.3 equivalents, from 1.0 equivalent to 2.0 equivalents, or from 1.0 equivalent to 1.5 equivalents, relative to the amount of the fatty acids in the raw material composition. When the ratio of the alkali catalyst to the raw material composition is in this range, reaction can be efficiently proceeded to obtain the free LC-PUFA.

The reaction solution may contain a component other than the substances described above in the range that does not impair progression of the alkali hydrolysis reaction. Examples of the component include antioxidants, such as tocopherol, vitamin C, and vitamin C derivatives, and non-alcohol solvents, such as acetone.

The hydrolysis treatment in this manufacturing method is performed in a temperature condition at 10° C. or lower. Because the hydrolysis treatment is performed at 10° C. or lower, generation or increase in at least one impurity selected from the group consisting of conjugated unsaturated fatty acids and coloring substances during the hydrolysis step can be suppressed. The temperature condition of the hydrolysis treatment needs to be a temperature range that can proceed the hydrolysis treatment as long as the temperature condition is at 10° C. or lower. For example, the temperature condition can be at −20° C. or higher, −10° C. or higher, −5° C. or higher, −4° C. or higher, −2° C. or higher, 0° C. or higher, or 2° C. or higher and can be at 8° C. or lower or 7° C. or lower. The temperature range of the hydrolysis treatment may be a numerical range of a combination of any upper limit value and any lower limit value described above. For example, the temperature range may be from −20° C. to 10° C., from −10° C. to 10° C., from −5° C. to 10° C., from −4° C. to 10° C., from 0° C. to 10° C., from 0° C. to 8° C., or from 2° C. to 7° C. When the hydrolysis treatment is performed in such a temperature condition at 10° C. or lower, generation or increase in the impurity described above can be further suppressed.

The reaction time of the alkali hydrolysis treatment differs depending on the set temperature range and, for example, the reaction time may be from 30 minutes to 600 hours, from 1 hour to 100 hours, from 8 hours to 80 hours, or from 19 hours to 25 hours. The amount of the fatty acid alkyl ester in the reaction solution decreases as the alkali hydrolysis treatment proceeds. Therefore, the alkali hydrolysis treatment can be terminated depending on the amount of the fatty acid alkyl ester remaining in the reaction solution. The amount of the fatty acid alkyl ester in the reaction solution can be identified by thin-layer chromatography (TLC), high performance liquid chromatography (HPLC), or the like.

The alkali hydrolysis treatment can be terminated by adding an acid to the reaction solution. By the addition of the acid, the pH of the reaction solution becomes acidic. Thus, the progression of the hydrolysis reaction is terminated, and a saponified product produced by the addition of the alkali catalyst is decomposed, thereby obtaining a free fatty acid. At this time, the free fatty acid, which is obtained by the termination treatment of the reaction, can be extracted by allowing an organic solvent such as hexane to be present in the reaction solution. Temperature conditions of the reaction termination and the extraction treatment are not particularly limited and, for example, the temperature conditions may be in a range of 0° C. to 40° C., 5° C. to 35° C., or 15° C. to 30° C. Timing of the reaction termination and the extraction treatment are not particularly limited and may be at the time when the reaction solution mixed by agitation or the like is separated into layers and stabilized.

The acid used for the termination of the alkali hydrolysis reaction is publicly known in the art, and examples of the acid include inorganic acids, such as hydrochloric acid, sulfuric acid, phosphoric acid, nitric acid, and carbonic acid, or organic acids, such as acetic acid, citric acid, and oxalic acid. As the acid, an inorganic acid is preferable from the perspective of ease in removal by water washing due to its high solubility to water. In particular, the acid is more preferably hydrochloric acid or the like because the amount of addition needs to be only a small amount and because generated salts and remaining acid can be removed. The added amount of the acid needs to be an amount that is effective in terminating the alkali hydrolysis treatment and may be approximately 1.1 equivalents relative to the amount of the added alkali catalyst.

The pH of the reaction solution after the acid addition needs to be a pH that can terminate the alkali hydrolysis, and the lower limit value thereof may be pH 1.0, pH 1.5, or pH 2.0 while the upper limit value thereof may be pH 6.0, pH 5.0, pH 4.5, or pH 4.0. The pH of the reaction solution after the acid addition may be, for example, from pH 1.0 to pH 6.0, from pH 1.5 to pH 4.5, from pH 2.0 to pH 5.0, and from 2.0 to 4.0. When the pH of the reaction solution after the acid addition is set in a range that is greater than pH 1, for example, pH 1.5 to pH 4.5 or pH 2.0 to pH 4.0, progression of a reverse reaction that may generate fatty acid alkyl esters after the termination of the hydrolysis reaction is suppressed, and increase in fatty acid alkyl esters can be suppressed. The pH of the reaction solution herein means a pH of an aqueous layer in the reaction solution containing an organic layer and the aqueous layer.

This manufacturing method may include a washing step of removing a water-soluble component from the reaction solution obtained after the reaction termination and the extraction treatment. In the washing step, water or the like may be used as a wash liquid and added to the reaction solution. The washing step may be performed until the pH of the wash liquid used in the washing treatment reaches approximately neutral, for example, greater than 6. The temperature of the washing step is not particularly limited, and the washing step may be performed at 25° C. or lower. After the washing step, this manufacturing method may include a recovery step that recovers the target free LC-PUFA-containing composition from the organic layer of the reaction solution after the washing treatment. The recovering treatment may employ techniques typically used for this purpose and, for example, may use an evaporator or the like.

The free LC-PUFA-containing composition obtained by this manufacturing method has a lower content of conjugated unsaturated fatty acids and/or coloring substances than the content of the case where hydrolysis treatment is performed at a temperature of higher than 10° C. In the free LC-PUFA-containing composition obtained by this manufacturing method, the content of the LC-PUFA may be, for example, 80.0% or greater, 85.0% or greater, 90.0% or greater, 95% or greater, 97.0% or greater, 98.0% or greater, 99.0% or greater, or 99.5% or greater, of the fatty acids in the composition. In the free LC-PUFA-containing composition obtained by this manufacturing method, the content of conjugated unsaturated fatty acids is an amount that is lower than the amount of the case where hydrolysis treatment is performed at a temperature of higher than 10° C. and, for example, may be 1.0% or less, 0.8% or less, 0.7% or less, 0.6% or less, 0.5% or less, 0.4% or less, or 0.3% or less, of the fatty acids in the composition. In the free LC-PUFA-containing composition obtained by this manufacturing method, the Gardner color as an indicator of coloring substances is a value that is lower than the value of the case where hydrolysis treatment is performed at a temperature of higher than 10° C. and, for example, may be less than 3+, 3− or less, 2+ or less, 2 or less, 1+ or less, or 1−. Examples of such a free LC-PUFA-containing composition include free LC-PUFA-containing compositions in other embodiments of the present disclosure described above.

The free LC-PUFA-containing composition has a smaller amount of remaining enzyme that has undergone heat inactivation treatment compared to the amount in a free LC-PUFA-containing composition obtained by using a hydrolysis enzyme. Effect of the remaining enzyme can be reduced with the composition having a smaller amount the remained heat-inactivated enzyme.

The free LC-PUFA-containing composition can have a low amount of residual organic solvent because the free LC-PUFA-containing composition is derived from a bio-oil and can be obtained without undergoing a step of chemical synthesis. The organic solvent in the present specification means an organic solvent other than fatty acids and means a hydrophobic or hydrophilic solvent having at least one carbon. Examples of the organic solvent include polar solvents, nonpolar solvents, water-miscible solvents, water-immiscible solvents, and combinations or at least two of these. Examples of the organic solvent include substituted or unsubstituted, saturated or unsaturated aliphatic hydrocarbons, aromatic hydrocarbons, alcohols, ethers, ketones, aldehydes, carboxylic acids, esters, nitriles, amides and the like. The organic solvent may be one type of these or a combination of at least two of these.

The total content of the residual organic solvent in the free LC-PUFA-containing composition may be 5000 ppm or less, 3000 ppm or less, 2000 ppm or less, or 1000 ppm or less.

The free LC-PUFA-containing composition may have a low content of at least one selected from the group consisting of methanol, ethanol, acetone, and hexane among the residual organic solvents. The content of these organic solvent may be each independently 500 ppm or less, 300 ppm or less, or 200 ppm or less. For example, all of the contents of methanol, ethanol, acetone, and hexane in the free LC-PUFA-containing composition may be 500 ppm or less, 300 ppm or less, or 200 ppm or less.

Because the free LC-PUFA-containing composition contains a smaller amount of impurities described above and contains a high concentration of at least one free LC-PUFA, functions corresponding to the type of the LC-PUFA contained can be favorably exhibited at high levels, and the free LC-PUFA-containing composition can be preferably used for various purposes.

Examples of preferable applications of the free LC-PUFA-containing composition include usage in food products, supplements, medicaments, cosmetics, and animal feed and usage in the manufacturing methods therefor. In particular, the free LC-PUFA-containing composition may be preferably used in medicaments containing a composition containing the LC-PUFA as an active ingredient. For example, when this free LC-PUFA-containing composition is a composition containing free ARA, free DGLA, free EPA, free DHA, or the like, the free LC-PUFA-containing composition can be significantly advantageously applied for the purposes requiring high productivity and high content of these functional LC-PUFA. Examples of such purposes include food products, supplements, medicaments, cosmetics, animal feed, and the like that are expected to exhibit effect on prevention of lifestyle-related diseases, such as arteriosclerosis, cerebral infarction, myocardial infarction, thrombosis, and hyperlipemia, improvement of metabolic syndrome, antiallergy, antiinflammation, anticancer, improvement in brain functions. Examples of the medicament include external medicines for skin, oral preparations and the like.

When the free LC-PUFA-containing composition is used as a medicament, the medicament contains the free LC-PUFA-containing composition and a pharmaceutically acceptable carrier and, as necessary, other components. The dosage form may be any form that is convenient for oral administration or parenteral administration based on the type of the LC-PUFA in the composition. Examples of the dosage form include injections, transfusions, powders, granules, tablets, capsules, enteric coated tablets, troches, peroral liquid preparations, suspensions, emulsions, syrups, liquids for external use, fomentations, nasal preparations, eardrops, eye drops, inhalants, ointments, lotions, suppositories and the like. These may be used individually or in combination depending on the symptoms.

By normal methods, these various types of preparations, according to a purpose, may be formulated by adding, to the principle agent, previously known adjutants commonly used in the field of drug preparation technology, as exemplified by excipients, binders, preservatives, stabilizers, disintegrants, lubricants, flavoring agents, or the like. Furthermore, in the case of oral administration for an adult, typically, the dosage for administration can be appropriately adjusted in a range of 0.01 mg to 10 g, preferably 0.1 mg to 2 g, and more preferably 1 mg to 200 mg, per day as the total amount of the LC-PUFA as a structured lipid. In the case of parenteral administration, the dosage for administration can be appropriately adjusted in a range of 0.001 mg to 1 g, preferably 0.01 mg to 200 mg, and more preferably 0.1 mg to 100 mg, per day as the total amount of the LC-PUFA as a structured lipid. However, these dosages differ depending on purpose of the administration, type of the LC-PUFA in the composition, and conditions of the person subjected to the administration (sex, age, weight, and the like).

EXAMPLES

The present disclosure is described below in detail using examples. However, the present disclosure is not limited in any manner by these examples.

In the examples and comparative examples in the section below, the LC-PUFA refers only to particular types; however, the type of the LC-PUFA is not particularly limited.

"Purified water" used in the section of examples below means water that has been purified, and "water" means tap water.

It was supposed that most of the fatty acids contained in the fatty acid alkyl ester-containing composition used in the examples as a raw material composition is in a fatty acid alkyl ester form. Consequently, the fatty acids contained in the samples are all described below as fatty acids in the alkyl ester form. However, this does not completely negate the fact that fatty acids in a form other than an alkyl ester form are included.

Comparative Example 1

Preparation Method

A raw material EPA ethyl ester 1 derived from a fish oil containing 96.7% of EPA was alkali-hydrolyzed by a conventional method.

That is, to 2.50 g of the raw material EPA ethyl ester 1, 6.25 mL of ethanol (4.92 g, 14.11 equivalents relative to the amount of fatty acids), 1.00 mL of water, and 0.76 g of 48 wt. % sodium hydroxide aqueous solution (1.20 equivalents of base relative to the amount of fatty acids) were added to prepare a sample solution 1. In the sample solution 1, the water content was 1.40 g. that is, 10.27 equivalents relative to the amount of fatty acids. The sample solution 1 was heated by an oil bath at 70° C. for 24 hours to perform hydrolysis treatment. In Table 1, the composition used during the preparation of the sample solution 1 is shown. In Table 1, the raw material composition indicates the weight (g) in the sample solution, and amounts of base, ethanol, and water indicates amounts relative to the amount of fatty acids in the raw material composition (molar equivalent). Note that, in the sample solution after the hydrolysis reaction, the amount of ethanol relative to the amount of fatty acids may be, theoretically, increased by at most 1 equivalent. In the sample solution after the hydrolysis reaction, the amount of water relative to the amount of fatty acids may be, theoretically, decreased by at most 1 equivalent. This is the same hereafter.

The termination of the hydrolysis treatment reaction was determined as follows. That is, a part of the sample solution 1 was taken out and combined and mixed in the ratio, sample solution: 1N hydrochloric acid aqueous solution:hexane=1: 2:5 (v/v/v). The separated hexane layer was used as a sample for identification.

Onto a TLC plate, 0.5 µL of the sample for identification was loaded by using a microsyringe and developed in a developing chamber. After the development, the thin-layer plate was taken out from the developing chamber, the solvent was vaporized in a fume hood, and a p-anisaldehyde coloring reagent was applied by dipping. After the application, heating was performed at approximately from 110° C. to 120° C. until color developed, thereby obtaining a spot. Disappearance of the spot of the raw material ethyl ester was visually observed and used as the point of reaction termination. This is the same hereafter.

As the development solvent, a solvent in which hexane: diethylether:acetic acid was 80:20:1 (v/v/v) was used. As the TLC plate, Silica gel 60G F254 (Merck Millipore) was used. As the coloring agent, a p-anisaldehyde coloring reagent was used.

The p-anisaldehyde coloring reagent was prepared as described below. That is, after 9.3 mL of p-anisaldehyde, 3.8 mL of acetic acid, and 340 mL of ethanol were mixed while being cooled with ice, 12.5 mL of concentrated sulfuric acid was mixed to the mixture to prepare the p-anisaldehyde coloring reagent.

The sample solution 1 after the treatment was air-cooled and transferred into a separatory funnel, and then 3.13 mL of hexane and 2.50 mL of purified water were added to this sample solution 1. After 2.25 g of hydrochloric acid was further added to the sample solution 1, the sample solution 1 was separated into two layers, a hexane layer and an aqueous layer. The pH of the aqueous layer was 1.0. In Table 1, the pH of the aqueous layer at this time was referred to as "pH at acidification". This is the same hereafter.

The sample solution 1 was agitated and then allowed to stand still. Then, after the aqueous layer was removed from the sample solution 1, 3.75 mL of purified water was further added to the sample solution 1 and agitated. An extremely small amount of hydrochloric acid was added to adjust the pH of the aqueous layer to 1.0. Thereafter, water washing was performed by using the same amount of purified water as a liquid for water washing. Water washing was repeated until the liquid for water washing collected after the water washing became neutral, pH 6.0 to 7.0. The hexane layer was recovered from the sample solution 1 after the water washing. From the recovered hexane layer, hexane was removed by an evaporator and vacuum drawing, and 2.12 g of EPA 1, which was a composition containing free EPA, was obtained.

Evaluation Method

The following evaluations were performed for the raw material EPA ethyl ester 1 and the EPA 1 obtained as described above. Among the evaluation results, Table 1 shows characteristics of the EPA 1, and Table 4 shows the fatty acid composition.

The recovery percentage was 96.8%. The Gardner color of the obtained EPA 1 was 6–, AnV was 1.9, the ethyl ester (EE) content was 2820 ppm, and the conjugated dienoic acid content was 2.45%. Conjugated unsaturated fatty acids other than the conjugated dienoic acid were not detected. Note that, for the conjugated unsaturated fatty acid, only the conjugated dienoic acid is shown in Table 1.

(1) Recovery Percentage

The recovery percentage of EPA of the EPA 1 was determined from the following equation. The molecular weight of the EPA ethyl ester as the raw material composition was 330.5028, and the molecular weight of the free EPA as the hydrolysate was 302.4498.

$$\text{recovery percentage (\%)} = \frac{\frac{\text{weight of hydrolysate (g)}}{\text{molecular weight of hydrolysate (g)}}}{\frac{\text{weight of raw material composition (g)}}{\text{molecular weight of raw material composition}}} \times 100 \qquad \text{[Equation 1]}$$

(2) Conjugated Unsaturated Fatty Acid

The measurement was performed based on Reference 1.14 of the Standard Methods for the Analysis of Fats, Oils, and Related Materials, 2013 Edition, established by Japan Oil Chemists' Society (JOCS).

(3) Color

The Gardner color was determined based on 3.2.1.1 of the Standard Methods for the Analysis of Fats, Oils, and Related Materials, 2013 Edition, established by Japan Oil Chemists' Society (JOCS).

(4) Anisidine Value

The anisidine value was determined based on 2.5.3 of the Standard Methods for the Analysis of Fats, Oils, and Related Materials, 2013 Edition, established by Japan Oil Chemists' Society (JOCS).

(5) Fatty Acid Composition

Fatty acid compositions of the raw material EPA ethyl ester 1 and the EPA 1 were determined from each fatty acid peak obtained by gas chromatography performed in the condition described below. Note that, for the EPA 1, methyl esterification was performed before the gas chromatography analysis. The methyl esterification was performed in accordance with American Oil Chemists' Society (AOCS) Official Method Ce 1b-89. Gas chromatography analysis conditions Instrument: Agilent 7890 GC system (Agilent Technologies)
Column: DB-WAX (Agilent Technologies, 30 m×0.25 mm ID, 0.25 μm film thickness) J&W122-7032
Column oven: 180° C.-3° C./min-230° C. (25 min)
Injection temperature: 250° C.
Injection method: split
Split ratio: 30:1
Detector temperature: 270° C.
Detector: FID
Carrier gas: helium (1.0 mL/min, constant flow)

(6) Fatty Acid Ethyl Ester Content

The measurement was performed by high performance liquid chromatography (HPLC) in the following conditions. A sample solution was prepared by diluting the EPA 1 with a 5 v/v % acetic acid/acetone solution under a condition that the concentration of the EPA 1 became 10 mg/mL. For the quantification, the measurement was performed by using a product containing 99% EPA ethyl ester and appropriately creating a calibration curve. HPLC measurement conditions Column: YMC_ODS-A column (4.6 mm×150 mm)
Eluent: MeOH:water=9:1
Flow rate: 1 mL/min
Column temperature: 40° C.
Injection amount: 5 μL was injected
Detector: UV 205 nm Comparative Example 2

Alkali hydrolysis was performed in the same manner as in Comparative Example 1 except for changing the amount of the raw material EPA ethyl ester 1 containing 96.7% of EPA of Comparative Example 1 and the amount of the ethanol in the sample solution to the amounts described below.

That is, to 5.00 g of the raw material EPA ethyl ester 1, 3.50 mL of ethanol (2.75 g, 3.95 equivalents relative to the amount of fatty acids), 2.01 mL of water, and 1.51 g of 48 wt. % sodium hydroxide aqueous solution (1.20 equivalents of base relative to the amount of fatty acids) were added to prepare a sample solution 2. In the sample solution 2, the water content was 2.80 g, that is, 10.27 equivalents relative to the amount of fatty acids. The sample solution 2 was heated with an oil bath at 70° C. for 24 hours to perform hydrolysis treatment. After the confirmation of termination of the hydrolysis treatment reaction, the sample solution 2 after the treatment was air-cooled and transferred into a separatory funnel, and then 6.25 mL of hexane and 5.00 mL of purified water were added to this sample solution 2. After 2.02 g of hydrochloric acid was further added to the sample solution 2, the sample solution 2 was separated into two layers, a hexane layer and an aqueous layer. The pH of the aqueous layer was 3.0.

The sample solution 2 was agitated and then allowed to stand still. Then, after the aqueous layer was removed from the sample solution 2, 7.50 mL of purified water was further added to the sample solution 2 after the removal and agitated. An extremely small amount of hydrochloric acid was added to adjust the pH of the aqueous layer to 1.0. Thereafter, water washing was performed by using the same amount of purified water as a liquid for water washing. Water washing was repeated until the liquid for water washing collected after the water washing became neutral, pH 6.0 to 7.0. The hexane layer was recovered from the sample solution 2 after the water washing. From the recovered hexane layer, hexane was removed by an evaporator and vacuum drawing, and 4.17 g of EPA 2, which was a composition containing free EPA, was obtained.

For the raw material EPA ethyl ester 1 and the EPA 2 obtained as described above, the evaluations were performed in the same manner as for the EPA 1. The results are shown in Table 1 and Table 4.

The recovery percentage was 91.0%. The Gardner color of the obtained EPA 2 was 12, AnV was 5.3, the ethyl ester (EE) content was 191 ppm, and the conjugated dienoic acid amount was 1.12%. Conjugated unsaturated fatty acids other than the conjugated dienoic acid were not detected. Note that, for the conjugated unsaturated fatty acid, only the conjugated dienoic acid is shown in Table 1.

Example 1

Alkali hydrolysis was performed in the same manner as in Comparative Example 1 except for changing the temperature condition during the alkali hydrolysis of the raw material EPA ethyl ester 1 containing 96.7% of EPA of Comparative Example 1 to 6° C.

That is, to 2.50 g of the raw material EPA ethyl ester 1, 6.25 mL of ethanol (4.92 g, 14.11 equivalents relative to the amount of fatty acids), 1.00 mL of water, and 0.76 g of 48 wt. % sodium hydroxide aqueous solution (1.20 equivalents of base relative to the amount of fatty acids) were added to prepare a sample solution 3. In the sample solution 3, the water content was 1.40 g, that is, 10.27 equivalents relative to the amount of fatty acids. The sample solution 3 was agitated at 6° C. for 24 hours to perform hydrolysis treatment. After the confirmation of termination of the hydrolysis treatment reaction, the sample solution 3 after the treatment was returned to room temperature and transferred into a separatory funnel, and then 3.13 mL of hexane and 2.50 mL of purified water were added to this sample solution 3. After 2.25 g of hydrochloric acid was further added to the sample solution 3, the sample solution 3 was separated into two layers, a hexane layer and an aqueous layer. The pH of the aqueous layer was 1.0.

The sample solution 3 was agitated and then allowed to stand still. Then, after the aqueous layer was removed from the sample solution 3, 3.75 mL of purified water was further added in the sample solution 3 after the removal and agitated. An extremely small amount of hydrochloric acid was added to adjust the pH of the aqueous layer to 1.0. Thereafter, water washing was performed by using the same amount of purified water as a liquid for water washing. Water washing was repeated until the liquid for water washing collected after the water washing became neutral, pH 6.0 to 7.0. The hexane layer was recovered from the sample solution 3 after the water washing. From the recovered hexane layer, hexane was removed by an evaporator and vacuum drawing, and 2.14 g of EPA 3, which was a composition containing free EPA, was obtained.

For the EPA 3, the evaluations were performed in the same manner as for the EPA 1. The results are shown in Table 1 and Table 4.

The recovery percentage was 93.8%. The Gardner color of the obtained EPA 3 was 2–. AnV was 1.3, the ethyl ester (EE) content was 2790 ppm, and the conjugated dienoic acid content was 0.47%. Conjugated unsaturated fatty acids except the conjugated dienoic acid were not detected. These physical property values are shown in Table 1. Note that, for the conjugated unsaturated fatty acid, only the conjugated dienoic acid is shown in Table 1.

Example 2

Alkali hydrolysis was performed in the same manner as in Comparative Example 2 except for changing the temperature condition during the alkali hydrolysis of the raw material EPA ethyl ester 1 containing 96.7% of EPA of Comparative Example 1 to 6° C.

That is, to 5.00 g of the raw material EPA ethyl ester 1, 3.50 mL of ethanol (2.75 g, 3.95 equivalents relative to the amount of fatty acids), 2.01 mL of water, and 1.51 g of 48 wt. % sodium hydroxide aqueous solution (1.20 equivalents of base relative to the amount of fatty acids) were added to prepare a sample solution 4. In the sample solution 4, the water content was 2.80 g, that is, 10.27 equivalents relative to the amount of fatty acids. The sample solution 4 was agitated at 6° C. for 24 hours to perform hydrolysis treatment.

The sample solution 4 after the treatment was returned to room temperature and transferred into a separatory funnel, and then 6.25 mL of hexane and 5.00 mL of purified water were added to this sample solution 4. After 2.09 g of hydrochloric acid was further added to the sample solution 4, the sample solution 4 was separated into two layers, a hexane layer and an aqueous layer. The pH of the aqueous layer was 3.0.

The sample solution 4 was agitated and then allowed to stand still. Then, after the aqueous layer was removed from the sample solution 4, 7.50 mL of purified water was further added in the sample solution 4 after the removal and agitated. An extremely small amount of hydrochloric acid was added to adjust the pH of the aqueous layer to 1.0. Thereafter, water washing was performed by using the same amount of purified water as a liquid for water washing. Water washing was repeated until the liquid for water washing collected after the water washing became neutral, pH 6.0 to 7.0. The hexane layer was recovered from the sample solution 4 after the water washing. From the recovered hexane layer, hexane was removed by an evaporator and vacuum drawing, and 4.37 g of EPA 4, which was a composition containing free EPA, was obtained.

For the EPA 4, the evaluations were performed in the same manner as for the EPA 1. The results are shown in Table 1 and Table 4.

The recovery percentage was 95.4%. The Gardner color of the obtained EPA 4 was 1, AnV was 2.1, the ethyl ester (EE) content was 240 ppm, and the conjugated dienoic acid content was 0.39%. Conjugated unsaturated fatty acids except the conjugated dienoic acid were not detected. Note that, for the conjugated unsaturated fatty acid, only the conjugated dienoic acid is shown in Table 1.

Comparative Example 3

Alkali hydrolysis was performed in the same manner as in Comparative Example 2 except for using a raw material DGLA ethyl ester 1 that was derived from microorganisms and that contained 96.1% of DGLA.

That is, to 1.50 g of the raw material DGLA ethyl ester 1, 1.05 mL of ethanol (0.83 g, 4.00 equivalents relative to the amount of fatty acids), 0.61 mL of water, and 0.45 g of 48 wt. % sodium hydroxide aqueous solution (1.20 equivalents of base relative to the amount of fatty acids) were added to prepare a sample solution 5. In the sample solution 5, the water content was 0.84 g, that is, 10.40 equivalents relative to the amount of fatty acids. The sample solution 5 was heated by an oil bath at 70° C. for 24 hours to perform hydrolysis treatment.

After the confirmation of termination of the hydrolysis treatment reaction, the sample solution 5 after the treatment was air-cooled and transferred into a separatory funnel, and then 1.88 mL of hexane and 1.50 mL of purified water were added to this sample solution 5. After 0.60 g of hydrochloric acid was further added to the sample solution 5, the sample solution 5 was separated into two layers, a hexane layer and an aqueous layer. The pH of the aqueous layer was 3.0.

The sample solution 5 was agitated and then allowed to stand still. Then, after the aqueous layer was removed from the sample solution 5, 2.25 mL of purified water was further added in the sample solution 5 after the removal and agitated. An extremely small amount of hydrochloric acid was added to adjust the pH of the aqueous layer to 1.0. Thereafter, water washing was performed by using the same amount of purified water as a liquid for water washing. Water washing was repeated until the liquid for water washing collected after the water washing became neutral, pH 6.0 to 7.0. The hexane layer was recovered from the sample solution 5 after the water washing. From the recovered hexane layer, hexane was removed by an evaporator and vacuum drawing, and 1.19 g of DGLA 1, which was a composition containing free DGLA, was obtained.

For the raw material DGLA ethyl ester 1 and the DGLA 1 obtained as described above, the evaluations were performed in the same manner as for Comparative Example 2. The results are shown in Table 2 and Table 4. The recovery percentage was 86.4%. The Gardner color of the obtained DGLA 1 was 6–, AnV was 13.7, the ethyl ester (EE) content was 21 ppm, and the conjugated dienoic acid content was 1.03%. Conjugated unsaturated fatty acids except the conjugated dienoic acid were not detected. Note that, for the conjugated unsaturated fatty acid, only the conjugated dienoic acid is shown in Table 2.

Note that, to measure the fatty acid ethyl ester content, a sample solution was prepared by diluting the DGLA 1 with a 5 v/v % acetic acid/acetone solution under a condition that the concentration of the DGLA 1 became 10 mg/mL, and a calibration curve was created by using a product containing 99% DGLA ethyl ester. For the calculation of the recovery percentage, the molecular weight of the free DGLA as a hydrolysate was 306.48, and the molecular weight of the DGLA ethyl ester as a raw material composition was 334.53.

Example 3

Alkali hydrolysis was performed in the same manner as in Comparative Example 3 except for using a raw material DGLA ethyl ester 2 that was derived from microorganisms and that contained 96.1% of DGLA, and changing the temperature condition during the hydrolysis to 6° C. As a result, 1.31 g of DGLA 2, which was a composition containing free DGLA, was obtained.

For the raw material DGLA ethyl ester 2 and the DGLA 2 obtained as described above, the evaluations were performed in the same manner as for Comparative Example 3. The results are shown in Table 2 and Table 4. The recovery percentage was 95.2%. The Gardner color of the obtained DGLA 2 was 1–, AnV was 3.2, the ethyl ester (EE) content was 151 ppm, and the conjugated dienoic acid content was 0.24%. Conjugated unsaturated fatty acids except the conjugated dienoic acid were not detected. Note that, for the conjugated unsaturated fatty acid, only the conjugated dienoic acid is shown in Table 2.

Comparative Example 4

Alkali hydrolysis was performed in the same manner as in Comparative Example 1 except for using a raw material PUFA ethyl ester 1 that was derived from fish oil and that contained 39.0% of DHA and 47.8% of EPA.

That is, to 2.50 g of the raw material PUFA ethyl ester 1, 6.25 mL of ethanol (4.92 g, 14.53 equivalents relative to the amount of fatty acids), 1.02 mL of water, and 0.73 g of 48 wt. % sodium hydroxide aqueous solution (1.20 equivalents of base relative to the amount of fatty acids) were added to prepare a sample solution 7. In the sample solution 7, the water content was 1.40 g, that is, 10.57 equivalents relative to the amount of fatty acids. The sample solution 7 was heated with an oil bath at 70° C. for 24 hours to perform hydrolysis treatment.

The sample solution 7 after the treatment was air-cooled and transferred into a separatory funnel, and then 3.13 mL of hexane and 2.50 mL of purified water were added to this sample solution 7. Then, hydrochloric acid was further added to the mixture. The sample solution 7 was separated into two layers, a hexane layer and an aqueous layer, after the addition of the hydrochloric acid. The pH of the aqueous layer was 1.0.

The sample solution 7 was agitated and then allowed to stand still. Then, after the aqueous layer was removed from the sample solution 7, 3.75 mL of purified water was further added to the sample solution 7 after the removal and agitated. An extremely small amount of hydrochloric acid was added to adjust the pH of the aqueous layer to 1.0. Thereafter, water washing was performed by using the same amount of purified water as a liquid for water washing. Water washing was repeated until the liquid for water washing collected after the water washing became neutral, pH 6.0 to 7.0. The hexane layer was recovered from the sample solution 7 after the water washing. From the recovered hexane layer, hexane was removed by an evaporator and vacuum drawing, and 2.25 g of PUFA 1, which was a composition containing free DHA and free EPA, was obtained.

For the raw material PUFA ethyl ester 1 and the PUFA 1 obtained as described above, the evaluations were performed in the same manner as for Comparative Example 1. The results are shown in Table 3 and Table 4. The recovery percentage was 98.4%. The Gardner color of the obtained DGLA 1 was 7–, AnV was 2.1, and the conjugated dienoic acid content was 3.29%. Conjugated unsaturated fatty acids except the conjugated dienoic acid were not detected. Note that, for the conjugated unsaturated fatty acid, only the conjugated dienoic acid is shown in Table 3.

Note that, for the calculation of the recovery percentage, the average molecular weight of the fatty acids in the raw material PUFA ethyl ester 1 was 340.167, and the average molecular weight of the fatty acids in the obtained PUFA 1 was 312.167.

Example 4

Alkali hydrolysis was performed in the same manner as in Comparative Example 4 except for using a raw material PUFA ethyl ester 2 that was derived from fish oil and that contained 39.0% of DHA and 47.8% of EPA, and changing the temperature condition during the alkali hydrolysis to 6° C. As a result, 4.58 g of PUFA 2, which was a composition containing free PUFA, was obtained.

That is, to 5.00 g of the raw material PUFA ethyl ester 2, 3.50 mL of ethanol (2.75 g, 4.07 equivalents relative to the amount of fatty acids), 2.04 mL of water, and 1.47 g of 48 wt. % sodium hydroxide aqueous solution (1.20 equivalents of base relative to the amount of fatty acids) were added to prepare a sample solution 8. In the sample solution 8, the water content was 2.80 g, that is, 10.57 equivalents relative to the amount of fatty acids. The sample solution 8 was agitated at 6° C. for 24 hours to perform hydrolysis treatment.

After the confirmation of termination of the hydrolysis treatment reaction, the sample solution 8 after the treatment was air-cooled and transferred into a separatory funnel, and then 6.25 mL of hexane and 5.00 mL of purified water were added to this sample solution 8. Then, hydrochloric acid was further added to the mixture. The sample solution 8 was separated into two layers, a hexane layer and an aqueous layer. The pH of the aqueous layer was 3.0.

The sample solution 8 was agitated and then allowed to stand still. Then, after the aqueous layer was removed from the sample solution 8, 7.50 mL of purified water was further added in the sample solution 8 after the removal and agitated. An extremely small amount of hydrochloric acid was added to adjust the pH of the aqueous layer to 1.0. Thereafter, water washing was performed by using the same amount of purified water as a liquid for water washing. Water washing was repeated until the liquid for water washing collected after the water washing became neutral, pH 6.0 to 7.0. The hexane layer was recovered from the sample solution 8 after the water washing. From the recovered hexane layer, hexane was removed by an evaporator and vacuum drawing, and 4.58 g of PUFA 2, which was a composition containing free PUFA, was obtained.

For the raw material PUFA ethyl ester 2 and the PUFA 2 obtained as described above, the evaluations were performed in the same manner as for Comparative Example 4. The results are shown in Table 3 and Table 4. The recovery percentage was 99.7%. The Gardner color of the obtained PUFA 2 was 2+, AnV was 3.9, and the conjugated dienoic acid content was 0.65%. Conjugated unsaturated fatty acids except the conjugated dienoic acid were not detected. Note that, for the conjugated unsaturated fatty acid, only the conjugated dienoic acid is shown in Table 3.

Table 1 to Table 4 for Comparative Example 1 to Comparative Example 4 and Example 1 to Example 4 are shown below. In Table 1 to Table 3, "Conditions" means the conditions of the hydrolysis treatment, and "Characteristics" means the characteristics and physical properties of the obtained composition by the hydrolysis treatment. In the columns of comparative examples and examples of Table 1 to Table 3, the left side columns describe about the raw material compositions, and the right side columns describe about the compositions obtained by the hydrolysis treatment. In Table 1 to Table 3, "EE" is an abbreviation for ethyl ester, and "G color" indicates the Gardner color. In Table 4, "C18PUFA" means the total of the di- or higher-valent polyunsaturated fatty acid having 18 carbons. "Others" means substances that are fatty acids except the LC-PUFA and the C18PUFA and that are not written. The "Others" is a value calculated by subtracting the content of the LC-PUFA and the content of the C18PUFA from the numerical value of 100%. "n.d." means less than 0.01%.

TABLE 1

|  |  | Comparative Example 1 | | Comparative Example 2 | | Example 1 | | Example 2 | |
| --- | --- | --- | --- | --- | --- | --- | --- | --- | --- |
|  |  | EPA-EE 1 | EPA 1 | EPA-EE 1 | EPA 2 | EPA-EE 1 | EPA 3 | EPA-EE 1 | EPA 4 |
| Conditions | Temperature | — | 70° C. | — | 70° C. | — | 6° C. | — | 6° C. |
| Sample solution composition | Raw material composition | — | 2.5 g | — | 5.0 g | — | 2.5 g | — | 5.0 g |
|  | Base | — | 1.20 equivalents | — | 1.20 equivalents | — | 1.20 equivalents | — | 1.20 equivalents |
|  | Ethanol | — | 14.11 equivalents | — | 3.95 equivalents | — | 14.11 equivalents | — | 3.95 equivalents |
|  | Water | — | 10.27 equivalents | — | 10.27 equivalents | — | 10.27 equivalents | — | 10.27 equivalents |
|  | pH at acidification | — | 1 | — | 3 | — | 1 | — | 3 |
| Characteristics | LC-PUFA (%) | 97.24% | 96.15% | — | 96.78% | — | 97.07% | — | 97.01% |
|  | G color | 1− | 6− | 1− | 12 | 1− | 2− | 1− | 1 |
|  | AnV | 1.4 | 1.9 | 1.2 | 5.3 | 1.2 | 1.3 | 1.2 | 2.1 |
|  | EE content (ppm) | — | 2820 | — | 191 | — | 2790 | — | 240 |
|  | Conjugated dienoic acid (%) | 0.40 | 2.45 | 0.40 | 1.12 | 0.40 | 0.47 | 0.40 | 0.39 |
|  | Recovery percentage (%) | — | 96.8 | — | 91.0 | — | 93.8 | — | 95.4 |

TABLE 2

|  |  | Comparative Example 3 | | Example 3 | |
| --- | --- | --- | --- | --- | --- |
|  |  | DGLA-EE 1 | DGLA 1 | DGLA-EE 2 | DGLA 2 |
| Conditions | Temperature | — | 70° C. | — | 6° C. |
| Sample solution composition | Raw material composition | — | 1.5 g | — | 1.5 g |
|  | Base | — | 1.20 equivalents | — | 1.20 equivalents |
|  | Ethanol | — | 4.00 equivalents | — | 4.00 equivalents |
|  | Water | — | 10.40 equivalents | — | 10.40 equivalents |
|  | pH at acidification | — | 3 | — | 3 |
| Characteristics | LC-PUFA (%) | 97.47% | 97.02% | — | 97.22% |
|  | G color | 1− | 6− | 1− | 1− |
|  | AnV | 2.2 | 13.7 | 1.5 | 3.2 |
|  | EE content (ppm) | — | 21 | — | 151 |
|  | Conjugated dienoic acid (%) | 0.22 | 1.03 | 0.22 | 0.24 |
|  | Recovery percentage (%) | — | 86.4 | — | 95.2 |

TABLE 3

|  |  | Comparative Example 4 | | Example 4 | |
| --- | --- | --- | --- | --- | --- |
|  |  | PUFA-EE 1 | PUFA 1 | PUFA-EE 2 | PUFA 2 |
| Conditions | Temperature | — | 70° C. | — | 6° C. |
| Sample solution composition | Raw material composition | — | 2.5 g | — | 5.0 g |
|  | Base | — | 1.20 equivalents | — | 1.20 equivalents |
|  | Ethanol | — | 14.53 equivalents | — | 4.07 equivalents |
|  | Water | — | 10.57 equivalents | — | 10.57 equivalents |
|  | pH at acidification | — | 1 | — | 3 |

TABLE 3-continued

|  |  | Comparative Example 4 | | Example 4 | |
|---|---|---|---|---|---|
|  |  | PUFA-EE 1 | PUFA 1 | PUFA-EE 2 | PUFA 2 |
| Characteristics | LC-PUFA (%) | 90.19% | 89.36% |  | 90.20% |
|  | G color | 1− | 7− | 1− | 2+ |
|  | AnV | 2.7 | 2.1 | 2.5 | 3.9 |
|  | Conjugated dienoic acid (%) | 0.63 | 3.29 | 0.63 | 0.65 |
|  | Recovery percentage (%) | — | 98.4 | — | 99.7 |

TABLE 4

|  | EPA-EE 1 | Comparative Example 1 EPA 1 | Comparative Example 2 EPA 2 | Example 1 EPA 3 | Example 2 EPA 4 | DGLA-EE 1 | Comparative Example 3 DGLA 1 | Example 3 DGLA 2 | PUFA-EE 1 | Comparative Example 4 PUFA 1 | Example 4 PUFA 2 |
|---|---|---|---|---|---|---|---|---|---|---|---|
| C20:2 | 0.02% | n.d. | n.d. | n.d. | n.d. | n.d. | n.d. | n.d. | n.d. | n.d. | n.d. |
| C20:3n-6 | n.d. | n.d. | n.d. | n.d. | n.d. | 96.14% | 95.56% | 95.76% | n.d. | n.d. | n.d. |
| C20:4n-6 | 0.13% | 0.11% | 0.11% | 0.12% | 0.13% | 1.24% | 1.38% | 1.38% | 0.06% | 0.07% | 0.06% |
| C20:3n-3 | n.d. | n.d. | n.d. | n.d. | n.d. | 0.09% | 0.08% | 0.08% | n.d. | n.d. | n.d. |
| C20:4n-3 | 0.32% | 0.31% | 0.31% | 0.31% | 0.31% | n.d. | n.d. | n.d. | 0.16% | 0.16% | 0.16% |
| C20:5n-3 | 96.73% | 95.73% | 96.36% | 96.64% | 96.57% | n.d. | n.d. | n.d. | 47.77% | 47.29% | 47.40% |
| C21:5n-3 | 0.04% | n.d. | n.d. | n.d. | n.d. | n.d. | n.d. | n.d. | 0.35% | 0.36% | 0.34% |
| C22:5n-3 | n.d. | n.d. | n.d. | n.d. | n.d. | n.d. | n.d. | n.d. | 2.86% | 2.82% | 2.78% |
| C22:6n-3 | n.d. | n.d. | n.d. | n.d. | n.d. | n.d. | n.d. | n.d. | 38.99% | 38.66% | 39.46% |
| PUFA | 97.24% | 96.15% | 96.78% | 97.07% | 97.01% | 97.47% | 97.02% | 97.22% | 90.19% | 89.36% | 90.20% |
| C18PUFA | 0.10% | 0.05% | 0.05% | 0.05% | 0.05% | 0.82% | 0.80% | 0.80% | 0.20% | 0.15% | 0.13% |
| Others | 2.66% | 3.80% | 3.17% | 2.88% | 2.94% | 1.71% | 2.18% | 1.98% | 9.61% | 10.49% | 9.67% |

As shown in Table 1 to Table 3, all of the compositions of Examples 1 to 4, in which the alkali hydrolysis treatment was performed at 6° C., i.e. the EPA 3 and the EPA 4 containing free EPA, the DGLA 2 containing free DGLA, and the PUFA 2 containing free DHA and free EPA, had conjugated dienoic acid contents of 1.0% or less and the Gardner colors of less than 3+. In particular, it was confirmed that the conjugated dienoic acid underwent almost no change even when subjected to silica gel treatment. Meanwhile, in all of Examples 1 to 4, the contents of the conjugated dienoic acid were reduced to at most the half of the contents in the cases of Comparative Examples 1 to 4, in which the treatment was performed at 70° C.

Furthermore, in all of the compositions of Examples 1 to 3, the anisidine values were 5.0 or less, and the ethyl ester contents were 500 ppm (0.05 wt. %) or less. In all of the compositions of Example 1 to Example 4, the amount of methanol, the amount of ethanol, the amount of acetone, and the amount of hexane were all 200 ppm or less.

Between Example 1 and Example 2, the amount of the ethanol relative to the amount of the raw material composition in the sample solution and the pH at acidification were different. Compared to the EPA 3 containing the free EPA obtained in Example 1, the EPA 4 containing the free EPA obtained in Example 2 had even better Gardner color, even lower amount of the fatty acid ethyl ester, and even lower content of the conjugated dienoic acid.

In such a free LC-PUFA-containing composition, amount of impurities including conjugated dienoic acid and/or coloring substance was small, and the high content of the target LC-PUFA was achieved. Such a free LC-PUFA-containing composition can be favorably applied to the purposes, such as medical purpose.

Disclosure of JP 2015-170856 A filed on Aug. 31, 2015 is incorporated herein in its entirety by reference.

All documents, patent applications, and technical specifications stated in the present specification are incorporated by citation in the present specification to the same degree as if stated to be incorporated by reference specifically and individually.

What is claimed is:

1. A free polyunsaturated fatty acid-containing composition, comprising at least one free polyunsaturated fatty acid having 20 or more carbons in an amount that a content thereof is 80.0% or greater of fatty acids in the composition, wherein the free polyunsaturated fatty acid-containing composition satisfies at least one selected from the group consisting of conditions (1) and (2):
   (1) a content of a conjugated unsaturated fatty acid being from 0.001% to 1.0% of the fatty acids in the composition; and
   (2) the Gardner color being less than 3+.

2. The free polyunsaturated fatty acid-containing composition according to claim 1, wherein the free polyunsaturated fatty acid-containing composition has an anisidine value of 5.0 or less.

3. The free polyunsaturated fatty acid-containing composition according to claim 1, wherein a content of the fatty acid alkyl ester is 0.2% or less of the fatty acids in the composition.

4. The free polyunsaturated fatty acid-containing composition according to claim 1, wherein the content of the conjugated unsaturated fatty acid is from 0.01% to 0.8% of the fatty acids in the composition.

5. The free polyunsaturated fatty acid-containing composition according to claim 1, wherein the polyunsaturated fatty acid is at least one selected from the group consisting of eicosadienoic acid, dihomo-γ-linolenic acid, Mead acid, eicosatetraenoic acid, arachidonic acid, eicosapentaenoic acid, docosatetraenoic acid, docosapentaenoic acid, and docosahexaenoic acid.

6. The free polyunsaturated fatty acid-containing composition according to claim 1, wherein a total content of a residual organic solvent in the composition is 5000 ppm or less.

7. The free polyunsaturated fatty acid-containing composition according to claim 1, wherein a content of a di- or higher-valent polyunsaturated fatty acid having 18 carbons in the composition is 2.0% or less of the fatty acids in the composition.

* * * * *